United States Patent [19]

Boyle

[11] Patent Number: 4,608,379
[45] Date of Patent: Aug. 26, 1986

[54] ANTIFUNGAL COMPOSITION AND METHOD EMPLOYING PYRIDINIUM COMPOUNDS

[75] Inventor: John T. A. Boyle, Cookham, England

[73] Assignee: John Wyeth & Brother Limited, Maidenhead, England

[21] Appl. No.: 647,577

[22] Filed: Sep. 5, 1984

[30] Foreign Application Priority Data

Sep. 7, 1983 [GB] United Kingdom ................ 8323949

[51] Int. Cl.⁴ ...................... A01N 43/40; A01N 43/84
[52] U.S. Cl. .................................. 514/318; 514/212;
514/222; 514/227; 514/238; 514/240; 514/252;
514/343; 514/351; 514/352; 514/357; 544/60;
544/125; 544/360; 546/193; 546/194; 546/281;
546/300; 546/304; 546/312; 546/329; 546/334
[58] Field of Search ................ 514/212, 318, 343, 238,
514/240, 227, 222, 252, 351, 352, 357; 546/329

[56] References Cited

U.S. PATENT DOCUMENTS

2,255,077 9/1941 Middleton ............................ 546/229
2,686,784 8/1954 Finkelstein et al. ................ 546/229

OTHER PUBLICATIONS

*Chemical Abstracts*, 95:44740g (1981) [Beecken, Ger. Offen. 2,932,092, 2/26/81].
*Chemical Abstracts*, 96:81205 (1982) [Barni et al., *Helv. Chim. Acta* 1981, 64(6), 1943–8].
Phillips, A., *J. Org. Chem.*, 12, 333 (1947).
Mills, W., et al., *J. Chem. Soc.*, 121, 946 (1922).
Clemo, G., et al., *J. Chem. Soc.*, 1938, pp. 1454–1455.
Williams, J., et al., *J. Org. Chem.*, 28, 388 (1963).
Doja, M., et al., *J. Ind. Chem. Soc.*, 24, 301–306 (1947).
Doja, M., et al., *J. Ind. Chem. Soc.*, 19, 125–129, 377–384 (1942).
Doja, M., et al., *J. Ind. Chem. Soc.*, 23, 117–120 (1946).
Brooker, L., et al., *J. Am. Chem. Soc.*, 67, 1875 (1945).
Foley, G., et al., *Ann. N.Y. Acad. Sci.*, 76, 413–441 (1958).
Kolomoitsev, L., et al., *Mikrobiol. Zh. Akad. Nauk. Ukr. SSR.*, 25(5), 58–67 (1963).
Bahner, C., et al., *J. Am. Chem. Soc.*, 75, 4838 (1953).
Bahner, C., et al., *J. Am. Chem. Soc.*, 73, 3407 (1951).

*Primary Examiner*—Richard A. Schwartz
*Attorney, Agent, or Firm*—George Tarnowski

[57] ABSTRACT

Compounds containing a cation of formula Ia

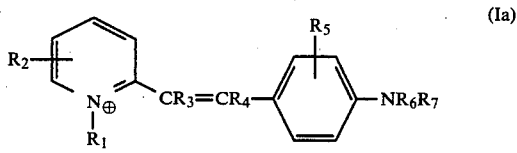

or its isomer Ib

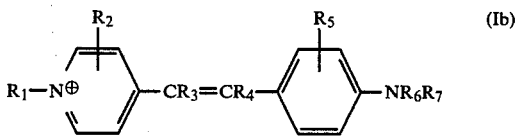

and a pharmaceutically acceptable anion are anti-fungal agents. In formula Ia and Ib $R_1$ is alkyl of at least 3 carbon atoms or aralkyl; $R_2$ and $R_5$ are hydrogen, lower alkyl, lower alkoxy, halogen or nitro; $R_6$ and $R_7$, when separate, are lower alkyl or aryl(lower)alkyl or, when joined together, are —(CH$_2$)$_2$—A—(CH$_2$)$_2$— (where A is —(CH$_2$)$_n$—, O, S or NR$_8$ where n is 0, 1 or 2 and $R_8$ is lower alkyl) or a mono- or di-(lower alkyl) substitution product thereof.

22 Claims, No Drawings

ANTIFUNGAL COMPOSITION AND METHOD EMPLOYING PYRIDINIUM COMPOUNDS

This invention relates to pyridinium compounds for use as anti-fungal agents. Some of the pyridinium compounds are novel per se. The invention also relates to a process of making the compounds and pharmaceutical compositions containing them.

The condensation between 4-dimethylaminobenzaldehyde and 1,2-dimethylpyridinium iodide was investigated by Mills and Pope [J. Chem. Soc., 121, 946 (1922)]. The product, 2-[4-(dimethylamino)styryl]-1-methylpyridinium iodide (hereinafer called compound A), was found to have a powerful sensitising action for green light upon the photographic plate. Condensation of the same aldehyde (4-dimethylaminobenzaldehyde) with 1,4-dimethylpyridinium iodide was investigated by Clemo and Swan [J. Chem. Soc., 1938, page 1454]. The condensation product, 4-[4-(dimethylamino)styryl]-1-methylpyridinium iodide, is hereinafter called compound B.

The 3-position isomer of compounds A and B, 3-[4-(dimethylamino)styryl]-1-methyl iodide, has been reported in the literature [J. Indian Chem. Soc., 24, 301–6 (1947)]. However, an attempt by the inventor to repeat the reported synthesis of the compound by treating 1,3-dimethylpyridinium iodide with 4-dimethylaminobenzaldehyde in refluxing ethanol with piperidine as catalyst failed to secure the reported product. The aldehyde was recovered unchanged. It is believed that the methyl group at the 3-position of the starting pyridinium compound is insufficiently activated to undergo the condensation.

A number of compounds related to compounds A and B have been disclosed in the literature. They include 2-[4-(dimethylamino)styryl]-5-ethyl-1-methylpyridinium iodide [see J. Org. Chem., 28, 388 (1963)]; 2-[4-(diethylamino)styryl]-1-methylpyridinium iodide (hereinafter referred to as compound C) [J. Org. Chem., 12, 333 (1947)]; 2-[4-(dimethylamino)styryl]-1-(iso-propyl, sec-butyl, iso-butyl or iso-amyl) pyridinium iodide [Chem. Abs., 41, 3102c (1947)]; 2-[4-(dimethylamino)styryl]-1-(ethyl, propyl or butyl) pyridinium iodide [Chem. Abs., 36, 6926[6] (1942)]; 2-[4-(diethylamino)styryl]-1-(ethyl, propyl or butyl) pyridinium iodide [Chem. Abs., 37, 4249[6] (1943)]; 2- or 4-[4-(diethylamino)styryl-1-n-hexylpyridinium bromide and 2- or 4-[4-(di-n-hexylamino)styryl]-1-n-hexylpyridinium bromide [U.S. Pat. No. 2,686,784]; 2-[4-(dimethylamino)styryl]-1-(dodecyl or octadecyl) pyridinium bromide [U.S. Pat. No. 2,255,077]; and 4-[4-(dimethylamino)styryl]-1-ethylpyridinium iodide (hereinafter referred to as compound D) [Chem. Abs., 40, 1519[5] (1946)].

The compounds designated as compounds A, B, C and D above have been reported to show inhibition of the fungus *Neurospora crassa* (wild type 4A) in Ann. N.Y. Acad. Sci., 76, 413–441 (1958) at page 440. However, when tested against other fungi these compounds may show no or little anti-fungal activity. In particular, our own results have found that compound A is not active against *Cryptococcus neoformans* (ATCC 14115). Moreover, compound B has been reported as inactive against *Epidermophyton rubrum, Microsporum lanosum* and *Trichophyton gypseum* in Mikrobiol. Zh. Akad. Nauk. Ukr. SSR., 25(5), 58–67 (1963). The four pyridinium compounds tested in the Ann. N.Y. Acad. Sci. reference have the characteristic that the substituent at the 1-position of the pyridine ring is methyl or ethyl. It has now been found that the potency against one or more fungi can be improved by using a substituent containing 3 or more carbon atoms at this position as is illustrated in Tables 1, 2 and 3 below.

The invention provides pyridinium compounds for use as pharmaceuticals, particularly as anti-fungal agents. The pyridinium compounds are those containing a cation having the formula Ia or Ib

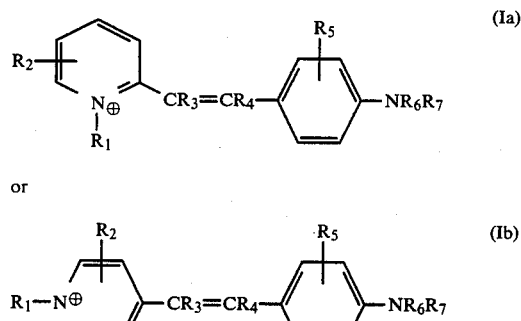

or

and a pharmaceutically acceptable anion. In formulae Ia and Ib $R_1$ represents alkyl containing at least 3 carbon atoms or aralkyl; $R_2$ and $R_5$ are independently hydrogen, lower alkyl, lower alkoxy, halogen or nitro; $R_3$ and $R_4$ are independently hydrogen or lower alkyl; and $R_6$ and $R_7$ are independently lower alkyl or aryl (lower) alkyl or $R_6$ and $R_7$, when joined together, represent a group having the formula II $$-(CH_2)_2-A-(CH_2)_2- \quad (II)$$

(where A is $-(CH_2)_n-$, O, S or $NR_8$ where n is 0, 1 or 2 and $R_8$ is lower alkyl) or a mono or di-(lower alkyl) substitution product thereof.

The term "lower" herein as applied to alkyl or alkoxy means that the alkyl or alkoxy group contains 1 to 6 carbon atoms, preferably 1 to 4 carbon atoms. As examples, there may be mentioned methyl, ethyl, propyl, isopropyl, butyl, pentyl and hexyl and methoxy, ethoxy, propoxy, isopropoxy, butoxy, pentoxy and hexoxy. The term "aryl (lower) alkyl" herein means lower alkyl (as defined above) monosubstituted by an aryl group, preferably a phenyl group. As examples benzyl and phenethyl may be mentioned.

The cations of formulae Ia and Ib are position isomers. The 4-position isomer, i.e. the cation of formula Ib, is preferred.

$R_1$ may be an alkyl group containing at least 3 carbon atoms, preferably 3 to 20 carbon atoms, for instance, propyl, isopropyl, butyl, pentyl, hexyl, heptyl, octyl, nonyl, decyl, undecyl, dodecyl, tetradecyl, hexadecyl, octadecyl and eicosyl. The alkyl group advantageously contains 3 to 12 carbon atoms. $R_1$ may also be arylalkyl, preferably aryl (lower) alkyl, advantageously benzyl or phenethyl. $R_3$ and $R_4$ are preferably hydrogen or methyl, advantageously hydrogen. $R_2$ and $R_5$ are independently hydrogen, lower alkyl or alkoxy (for instance as illustrated above), halogen (for instance chlorine or bromine) or nitro. $R_6$ and $R_7$, when separate, may be lower alkyl (for instance as illustrated above) or aryl (lower) alkyl, preferably phen (lower) alkyl, advantageously benzyl or phenethyl. $R_6$ and $R_7$, when separate, are most advantageously methyl or ethyl. $R_6$ and $R_7$ may be joined so that —NR$_6$R$_7$ represents pyrrolidino, piperidino, morpholino, thiomorpholino, 4-loweralkyl-piperazin-1-yl, preferably piperidino. The ring carbon atoms are optionally substituted by a total of up to two lower alkyl groups.

As examples of the pharmaceutically acceptable anion of the anti-fungal compound there may be mentioned a halide (for instance, chloride, bromide or iodide), sulphate, nitrate, phosphate, an organosulphonate (for instance methane-sulphonate or p-toluenesulphonate), acetate, maleate, citrate, fumarate, tartrate, malonate, or formate.

Some of the anti-fungal compounds of the invention are known per se. However, it is believed that none of the known compounds has been previously known for any therapeutic purpose.

The anti-fungal compounds that are novel per se include those containing a pharmaceutically acceptable anion and the cation of formula Ia or Ib where R$_1$, R$_2$, R$_3$ R$_4$, R$_5$, R$_6$ and R$_7$ are as defined above subject to the proviso that, if both R$_6$ and R$_7$ are lower alkyl, then R$_2$, R$_4$ and R$_5$ are not all hydrogen. The novel compounds of this invention especially include those where R$_2$ is lower alkyl and also those where R$_6$ and R$_7$ together represent formula II or a mono- or di- (lower alkyl) substitution product thereof.

The anti-fungal compounds of the invention are prepared by condensing a pyridinium compound containing a cation having the formula IIIa or IIIb

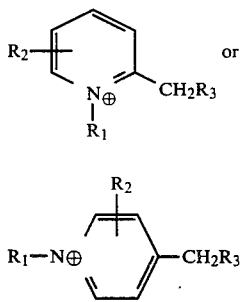

(where R$_1$, R$_2$ and R$_3$ are as defined above) with a carbonyl compound having the formula IV

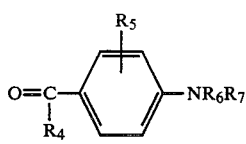

(where R$_4$, R$_5$, R$_6$ and R$_7$ are as defined above) or a reactive derivative of such a carbonyl compound. The condensation of the carbonyl compound with the compound containing the cation of formula IIIa or IIIb may be carried out in known manner, normally in the presence of a catalyst such as piperidine. Alternatively the condensation may be carried out with a reactive derivative of the carbonyl compound, for instance an imine having the formula VI

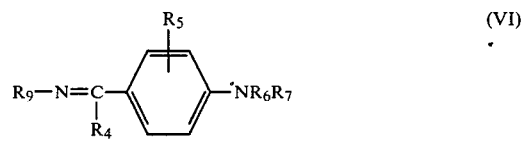

(where R$_4$, R$_5$, R$_6$ and R$_7$ are as defined above and R$_9$ is hydrogen or lower alkyl). The use of an imine is recommended particularly where R$_4$ is lower alkyl.

The anion of the compound containing the cation IIIa or IIIb is preferably the same as the pharmaceutically acceptable cation in the anti-fungal compound of the invention. Alternatively, the pharmaceutically acceptable anion may be incorporated by exchange of anions in known manner, as a subsequent step.

The anti-fungal compounds of the invention may be tested for activity by means of the following in vitro procedure.

Test substance is solubilised or suspended in appropriate reagent and further diluted in sterile distilled water to provide a range of concentrations from 200 to 10 μg/ml. 20 lambda portions are placed on sterile dried ¼" paper discs and allowed to dry for 20-30 minutes. Agar plates with a 10 ml base layer are seeded with the fungi in a 4 ml seed layer and allowed to solidify. The impregnated discs are then placed on the seeded agar surface and incubated for the time required for the particular culture.

The representative fungi are:
*Candida albicans* ATCC 10231 (CA)
*Cryptococcus neoformans* ATCC 14115 (CN)
*Histoplasma capsulatum* ATCC 11407—yeast phase (HC)
*Blastomyces dermatitidis* ATCC 28839—yeast phase (BD)
*Trichophyton mentagrophytes* ATCC 9533 (TM)

The letters in brackets represent an abbreviation used for identification in the Tables of results below. All five fungi are human pathogens; the first four cause serious systemic mycotic infections as well as local. The trychophyton culture is mainly a dermatophyte. Clotrimazole may be used as a control. Activity is indicated by size in mm. of any zones exhibited by the compounds. A compound is regarded as inactive where no zone is exhibited at the highest concentration tested (200 μg/ml).

Table 1 below illustrates the effect of increasing the number of carbon atoms in the alkyl group at the 1-position of the pyridine ring of 1-alkyl-2-[4-(dimethylamino)styryl pyridinium compounds of the formula VII

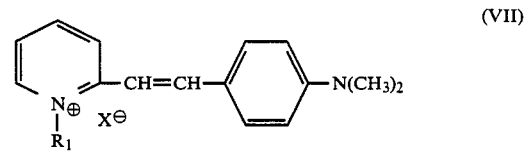

TABLE 1

| Compound Meanings of Symbols in Formula VII Illustrating invention or for comparison | | Compound A Comparison | Compound of Example 3 Invention | Compound of Example 5 Invention |
|---|---|---|---|---|
| | $R_1$ | methyl | hexyl | dodecyl |
| | $X^\ominus$ | iodide | bromide | bromide |
| Fungus Tested and Results | CA | 11 mm at 200 μg/ml | 10.8 mm at 200 μg/ml | 10 mm at 100 μg/ml |
| | CN | No activity | 26 mm at 100 μg/ml | 9 mm at 10 μg/ml |
| | TM | 10 mm at 200 μg/ml | 16.3 mm at 100 μg/ml | 8 mm at 100 μg/ml |
| | HC | 8 mm at 100 μg/ml | 15.3 mm at 100 μg/ml | 12.3 mm at 10 μg/ml |
| | BD | 13 mm at 100 μg/ml | 13 mm at 10 μg/ml | 8 mm at 10 μg/ml |

Table 1 shows that the 1-hexyl compound of the invention demonstrated anti-fungal activity at the same concentration as the 1-methyl comparison compound in the case of two fungi and at a lower concentration in the case of the other three fungi. The 1-dodecyl compound of the invention demonstrated an anti-fungal response at a lower concentration than the 1-methyl comparison compound in the case of all five fungi tested. Thus the increase in the number of carbon atoms in the 1-alkyl substituent tends to improve activity.

Table 2 below compares two 1-alkyl-2-(4-diethylaminostyryl)pyridinium compounds of the formula VIII

TABLE 2

$$\text{(VIII)}$$

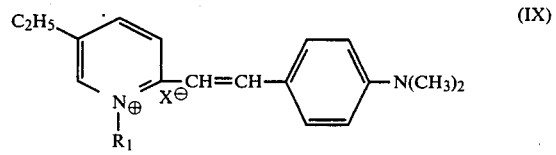

| Compound | | Compound C | Example 4 |
|---|---|---|---|
| Meaning of the symbols in formula VIII | $R_1$ | methyl | hexyl |
| | $X^\ominus$ | iodide | bromide |
| Fungus Tested and Results | CA | 10.3 mm at 200 μg/ml | 12 mm at 100 μg/ml |
| | CN | 10 mm at 100 μg/ml | 14 mm at 10 μg/ml |
| | TM | 10 mm at 100 μg/ml | 13 mm at 10 μg/ml |
| | HC | 10 mm at 100 μg/ml | 14 mm at 10 μg/ml |
| | BD | 9 mm at 10 μg/ml | 14 mm at 10 μg/ml |

Table 2 shows that the 1-hexyl compound of the invention showed an anti-fungal response at the same concentration as the 1-methyl comparison compound in the case of one fungus (BD) but exhibited activity at a lower concentration than the 1-methyl comparison compound in the case of the other four fungi. Again the increase in the number of carbon atoms in the 1-alkyl group tends to improve potency.

Table 3 below compares 1-propyl and 1-ethyl compounds having the formula IX

TABLE 3

$$\text{(IX)}$$

| Compound (Invention or Comparison) | | Comparison | Invention (Example 2) |
|---|---|---|---|
| Meaning of symbols in formula IX | $R_1$ | ethyl | propyl |
| | $X^\ominus$ | iodide | bromide |
| Fungus Tested and Results | CA | No activity | 10 mm at 100 μg/ml |
| | CN | 18.3 mm at 100 μg/ml | 11 mm at 100 μg/ml |
| | TM | No activity | 11.7 mm at 100 μg/ml |
| | HC | 9.5 mm at 100 μg/ml | 16.3 mm at 10 μg/ml |
| | BD | 11 mm at 100 μg/ml | 14.3 mm at 10 μg/ml |

In the case of fungus CN, the two compounds both exhibited a zone at the same concentration. In the case of the other four fungi, the 1-propyl compound exhibited zones at a lower concentration than the 1-ethyl compound.

Table 4 below presents results for other antifungal compounds of this invention.

TABLE 4

| Compound obtained in Example No. | Fungus | | | | |
|---|---|---|---|---|---|
| | CA | CN | TM | HC | BD |
| 1 | 12 mm at 100 μg/ml | 23.3 mm at 100 μg/ml | 19.3 mm at 100 μg/ml | 15 mm at 10 μg/ml | 12.7 mm at 10 μg/ml |
| 6 | 9 mm at 100 μg/ml | 9.3 mm at 100 μg/ml | 9 mm at 200 μg/ml | 9 mm at 10 μg/ml | 9 mm at 100 μg/ml |
| 7 | 9 mm at 100 μg/ml | 12 mm at 100 μg/ml | 9 mm at 100 μg/ml | 11.3 mm at 100 μg/ml | 7 mm at 10 μg/ml |
| 8 | 12.3 mm at 100 μg/ml | 18 mm at 100 μg/ml | 23.3 mm at 100 μg/ml | 10.3 mm at 10 μg/ml | 9 mm at 10 μg/ml |
| 9 | 8 mm at 100 μg/ml | 8.7 mm at 100 μg/ml | 8 mm at 10 μg/ml | 12 mm at 10 μg/ml | NOT TESTED |
| 10 | 10 mm at 10 μg/ml | 17.7 mm at 10 μg/ml | 10 mm at 10 μg/ml | 26 mm at 10 μg/ml | NOT TESTED |
| 11 | 15.3 mm at 10 μg/ml | 25.3 mm at 10 μg/ml | 23 mm at 10 μg/ml | 35 mm at 10 μg/ml | NOT TESTED |

The antifungal compounds of this invention may be administered internally (for instance orally) or topically in the form of compositions containing the compound in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable porportions and compacted in the shape and size desired. The powders and tablets preferably contain from 5 to 99, preferably 10-80% of the active ingredient. Suitable solid carriers are magnesium carbonate, magnesium stearate, talc, lactose, pectin, dextrin, starch, gelatin, tragacanth, methylcellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage form can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

Where the antifungal compound of the invention is to be administered topically it may be presented in the form of an aerosol, a semi-solid pharmaceutical composition, a powder or a solution. By the term "a semi-solid composition" there is meant an ointment, cream, salve, jelly or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Chapter 67 of Remington's Pharmaceutical Sciences, 15th Edition (1975) published by Mack Publishing Company.

Preferably, the topical compositions of the present invention contain from about 0.1% to about 20% by weight of the active ingredient. The compositions may, for example, contain from about 0.5% (preferably from about 1%) to about 10% by weight of the active ingredient.

The carrier used in the topical compositions of the present invention may be any carrier suitable for preparing topical semi-solid compositions or topical aerosol compositions. Examples of suitable carriers for semi-solid compositions are given in Lachman, Lieberman and Kanig (loc-cit) and in Chapter 67 of Remington's Pharmaceutical Sciences, (lot-cit). The carrier for the semi-solid composition may be, for example, an emulsion base of the oil in water class (e.g. an emulsion of soft and liquid paraffins in water). Alternatively, the carrier may be an absorption base (e.g. a mixture of wool fat and soft paraffin). A third class of suitable carriers are water miscible bases (e.g. mixtures of high and low molecular weight polyethylene glycols).

When the composition is in aerosol form for topical administration, the composition may comprise the active ingredient and an easily liquifiable gas. Examples of such liquifiable gases are halogenated hydrocarbons and liquified lower hydrocarbons, both of which are well known as propellants in the aerosol art. (By "lower hydrocarbon" is meant a hydrocarbon containing up to six carbon atoms).

In addition to the active ingredient and the carrier base, the topical compositions of the invention may contain other ingredients such as antioxidants, buffers, emulsifying agents, perfumes, preservatives and solvents which confer on the product properties desirable in a topical formulation.

As an example of a solution for topical administration there may be mentioned tinctures, in particular solutions of the active ingredient in alcohol or aqueous alcohol at concentrations of, for instance, 0.1%-1%.

The following Examples illustrate the preparation of antifungal compounds of this invention.

EXAMPLE 1

2-[4-(Diethylamino)styryl]-5-ethyl-1-propylpyridinium salt

5-Ethyl-2-methyl-1-propylpyridinium bromide (7.32 g, 0.03 mole) and 4-diethylaminobenzaldehyde (7.0 g, 0.04 mole) were refluxed for four hours in methanol (50 ml) in the presence of piperidine (1 ml) under nitrogen. On cooling and addition of ether no precipitate was obtained. The solution was evaporated to give a red oil which was dissolved in isopropanol and twice the volume of ether was added, when a red crystalline solid was obtained (5.4 g). 2 Grams were re-dissolved in isopropanol and isopropyl ether was added to give red crystals of 2-[4-(diethylamino)styryl]-5-ethyl-1-propylpyridinium bromide hemihydrate (1.6 g), melting point 165°-167° (decomposition).

Analysis Found: C, 63.9%, H, 7.77%; N, 6.44%. $C_{22}H_{31}BrN_2 \cdot \frac{1}{2}H_2O$ requires C, 64.1%, H, 7.82%, N, 6.79%.

EXAMPLE 2

2-[4-(Dimethylamino)styryl]-5-ethyl-1-propylpyridinium salt

5-Ethyl-2-methyl-1-propylpyridinium bromide (8.1 g, 0.033 mole) and 4-dimethylaminobenzaldehyde (6.0 g, 0.04 mole) were refluxed in methanol (50 ml) in the presence of piperidine (1.5 ml) under nitrogen for four hours. Ether was added to the cool solution and, on scratching, a red solid crystallised which was collected and washed with a little isopropanol to give 2-[4-(dimethylamino)-styryl]-5-ethyl-1-propylpyridinium bromide (7.7 g). Melting point 236°–237° (decomposition).

Analysis Found: C, 63.9%; H, 7.50%; N, 7.33%. $C_{20}H_{27}BrN_2$ requires C, 64.0%; H, 7.25%; N, 7.46%.

EXAMPLE 3

2-[4-(Dimethylamino)styryl]-1-hexylpyridinium salt

1-Hexyl-2-methylpyridinium bromide (7.8 g, 0.03 mole) and 4-dimethylaminobenzaldehyde (6.0 g, 0.04 mole) were refluxed in methanol (50 ml) in the presence of piperidine (1.0 ml) under nitrogen for four hours. On cooling and the addition of about 100 ml of ether a solid crystallised which was collected and washed with a little isopropanol to give 2-[4-(dimethylamino)styryl]-1-hexylpyridinium bromide (6.3 g), melting point 217°–218° (decomposition).

Analysis Found: C, 64.6%; H, 7.51%; N, 7.15%. $C_{21}H_{29}BrN_2$ requires C, 64.8%; H, 7.51%; N, 7.19%.

EXAMPLE 4

2-[4-(Diethylamino)styryl]-1-hexylpyridinium salt

1-Hexyl-2-methylpyridinium bromide (7.8 g, 0.03 mole) and 4-diethylaminobenzaldehyde (7.0 g, 0.04 mole) were refluxed in methanol (50 ml) in the presence of piperidine (1.0 ml) under nitrogen for four hours. The solution was evaporated and the resulting oil was redissolved in a small amount of isopropanol. Addition of twice the volume of ether gave a red crystalline solid which was collected and washed with isopropanol/ether to give 2-[4-(diethylamino)styryl]-1-hexylpyridinium bromide hemihydrate (5.8 g), melting point 222°–223° (decomposition).

Analysis Found: C, 65.0%, H, 7.73%, N, 6.46%. $C_{23}H_{33}BrN.\frac{1}{2}H_2O$ requires C, 64.8%; H, 8.04%; N, 6.57%.

EXAMPLE 5

2-[4-(dimethylamino)styryl-1-dodecylpyridinium salt

1-Dodecyl-2-methylpyridinium bromide (3.42 g, 0.01 mole) and 4-dimethylaminobenzaldehyde (1.6 g, 0.011 mole) were refluxed in ethanol (15 ml) in the presence of piperidine (0.2 ml) under nitrogen for two hours. The solution was cooled and ether was added when an orange solid crystallised which was collected giving 2-[4-(dimethylamino)styryl]-1-dodecylpyridinium bromide quarter hydrate (2.4 g), melting point 197°–198° C.

Analysis Found: C, 67.7%; H, 8.97%; N, 5.85%. $C_{27}H_{41}BrN_2.\frac{1}{4}H_2O$ requires C, 67.8%; H, 8.75%; N, 5.86%.

EXAMPLE 6

2-[4-(Diethylamino)styryl]-1-dodecylpyridinium salt

1-Dodecyl-2-methylpyridinium bromide (3.42 g), 0.01 mole) and 4-diethylaminobenzaldehyde (1.9 g), 0.011 mole) were refluxed in ethanol (15 ml) in the presence of piperidine (0.2 ml) under nitrogen for two hours. The solution was cooled and ether was added when an orange solid crystallised which was collected giving 2-[4-(diethylamino)styryl]-1-dodecylpyridinium bromide hemihydrate, (2.1 g), melting point 199°–200° C.

Analysis Found: C, 68.4%; H, 9.13%; N, 5.35%. $C_{29}H_{45}BrN_2.\frac{1}{2}H_2O$ requires C, 68.2%, H, 9.08%; N, 5.4%.

EXAMPLE 7

1-Benzyl-2-[4-(dimethylamino)styryl]pyridinium salt

2-Picoline (9.3 g, 0.1 mole) and benzyl bromide (17.1 g, 0.1 mole) were refluxed in isopropanol (50 ml) overnight. The solvent was evaporated giving an oil which was heated at 100° C. for six hours. The resulting crude oil (8.0 g, 0.03 mole) and 4-dimethylaminobenzaldehyde (4.6 g, 0.03 mole) were refluxed in methanol (50 ml) in the presence of piperidine (0.2 ml) under nitrogen for three hours. On cooling dark-coloured crystals were obtained which were collected to give 1-benzyl-2-[4-(dimethylamino)styryl]pyridinium bromide (6.8 g), melting point 250°–251° C.

Analysis Found: C, 66.9%; H, 5.99%; N, 6.77%. $C_{22}H_{23}BrN_2$ requires C, 66.8%; H, 5.86%; N, 7.09%.

EXAMPLE 8

1-Benzyl-2-[4-(diethylamino)styryl]pyridinium salt

2-Picoline (9.3 g, 0.1 mole) and benzyl bromide (17.1 g, 0.1 mole) were refluxed in isopropanol (50 ml) overnight. The solvent was evaporated giving an oil which was heated at 100° C. for six hours. The resulting crude oil (8.5 g, 0.032 mole) and 4-diethylaminobenzaldehyde (6.0 g, 0.033 mole) were refluxed in methanol (40 ml) in the presence of piperidine (0.2 ml) under nitrogen for three hours. On cooling dark-coloured crystals were obtained which were collected to give 1-benzyl-2-[4-(diethylamino)styryl]pyridinium bromide (6.2 g), melting point 231°–233° C.

Analysis Found: C, 67.8%; H, 6.41%; N, 6.38%. $C_{24}H_{27}BrN_2$ requires C, 68.1%; H, 6.43%; N, 6.62%.

EXAMPLE 9

1-Dodecyl-2-[(4-piperidino)styryl]pyridinium salt

1-Dodecyl-2-methylpyridinium bromide (2.3 g, 0.0067 mole) and 4-piperidinobenzaldehyde (1.27 g, 0.0067 mole) were refluxed in methanol (20 ml) in the presence of piperdine (0.1 ml) under nitrogen for three hours. The solution was cooled and addition of ether gave a crystalline solid which was collected giving 1-dodecyl-2-[(4-piperidino)styryl]pyridinium bromide (0.85 g), melting point 203°–205° C.

Analysis Found: C, 70.0%; H, 8.82%; N, 5.79%. $C_{30}H_{45}BrN_2$ requires C, 70.2%, H, 8.83%, N, 5.45%.

EXAMPLE 10

1-Hexyl-2-[(4-piperidino)styryl]pyridinium salt

2-Picoline (2.79 g, 0.03 mole) and 1-bromo-hexane (5.0 g, 0.03 mole) were heated in an oil bath at 130° C. for five hours. The resulting oil was cooled and dissolved in methanol (40 ml). 4-Piperidinobenzaldehyde (5.67 g, 0.03 mole) and piperidine (0.25 ml) were added and the mixture was refluxed under nitrogen for two hours. The addition of about 100 ml of ether to the cold solution gave red crystals which were collected and washed to give 1-hexyl-2-[(4-piperidino)styryl]-pyridinium bromide (2.1 g), melting point 212°–214° C. (decomposition).

Analysis Found: C, 66.6%; H, 7.77%; N, 6.42%. $C_{24}H_{33}BrN_2.\frac{1}{4}H_2O$ requires C, 66.4%; H, 7.80%; N, 6.50%.

EXAMPLE 11

4-[4-(Dimethylamino)styryl]-1-hexylpyridinium salt

4-Picoline (2.79 g, 0.03 mole) and 1-bromohexane (4.25 ml, 0.03 mole) were heated in an oil bath at 130° C. for 2 hours. The resulting brown oil was cooled. Methanol (40 ml), 4-dimethylaminobenzaldehyde (4.5 g, 0.03 mole) and piperdine (0.25 ml) were added. The mixture was refluxed for 3 hours and cooled. A large volume of ether was added to form a crystalline product which was recrystallised by dissolving in isopropyl alcohol and adding ether to give crystals of 4-[4-(dimethylamino)styryl]-1-hexylpyridinium bromide quarter hydrate (2.2 g), melting point 224°–226° C. (decomposition). The compound exhibited infra-red spectral bands at 720, 815, 835, 883, 940, 987, 1158, 1330, 1362, 1522, 1575 and 1640 wavenumbers.

Analysis Found: C, 64.0%; H, 7.58%; N, 7.20%. $C_{21}H_{29}BrN_2.\frac{1}{4}H_2O$ requires C, 64.0%; H, 7.55%; N, 7.11%.

EXAMPLE 12

4-[4-(diethylamino)styryl]-1-hexylpyridinium salt

By using a similar procedure to Example 11 with 4-diethylaminobenzaldehyde instead of 4-dimethylaminobenzaldehyde, 4-[4-(diethylamino)styryl]-1-hexylpyridinium bromide hemihydrate, melting point 203°–5° C. was prepared. The compound exhibited infra-red spectral bands at 703, 729, 813, 829, 891, 1001, 1047, 1076, 1153, 1175, 1192, 1269, 1354, 1401, 1517, 1577 and 1641 wavenumbers.

EXAMPLE 13

1-Hexyl-4-[4-(piperidino)styryl]pyridinium salt

By using a similar procedure to Example 11 with ethanol instead of methanol and 4-piperidinobenzaldehyde instead of 4-dimethylaminobenzaldehyde, 1-hexyl-4-[4-(piperidino)styryl]pyridinium bromide quarter hydrate was prepared. The compound exhibited infra-red spectral bands at 722, 846, 889, 946, 992, 1168, 1227, 1335, 1526, 1592 and 1642 wavenumbers.

EXAMPLE 14

4-[4-(dimethylamino)styryl]-1-dodecylpyridinium salt

By using a similar procedure to Example 11 with 1-bromododecane instead of 1-bromohexane, 4-[4-(dimethylamino)styryl]-1-dodecylpyridinium bromide is prepared.

EXAMPLE 15

1-Decyl-4[4-(Dimethylamino)styryl]pyridinium salt

The title compound bromide salt was prepared by using a similar procedure to Example 11 with 1-bromodecane instead of 1-bromohexane and ethanol instead of methanol. The compound obtained exhibited infra-red spectral bands at 722, 846, 889, 946, 992, 1168, 1227, 1335, 1526, 1592 and 1642 wavenumbers.

EXAMPLE 16

1-Hexyl-4-[4-(pyrrolidin-1-yl)styryl]pyridinium salt

The title compound bromide salt hemihydrate was prepared in a similar manner to Example 13 using 4-(pyrrolidin-1-yl)benzaldehyde instead of 4-piperidinobenzaldehyde. The compound obtained exhibited infra-red spectral bands at 726, 814, 832, 962, 999, 1045, 1173, 1189, 1211, 1332, 1524, 1589 and 1642 wavenumbers.

EXAMPLE 17

1-Decyl-4-[4-pyrrolidin-1-yl)styryl]pyridinium salt

The title compound bromide salt was prepared in a similar manner to Example 16 using 1-bromodecane instead of 1-bromohexane and exhibited infra-red spectral bands at 723, 847, 888, 1000, 1177, 1210, 1333, 1526, 1592 and 1642 wavenumbers.

EXAMPLE 18—TOPICAL FORMULATIONS

| (A) Oil in water emulsion base | % w/w |
|---|---|
| Compound of Example 11 (active compound) | 1-2 |
| White soft paraffin | 15.0 |
| Liquid paraffin | 6.0 |
| Cetostearyl alcohol | 7.2 |
| Cetomacragol 1000 | 1.8 |
| Benzyl alcohol | 1.5 |
| Propyl hydroxybenzoate | 0.08 |
| Methyl hydroxybenzoate | 0.15 |
| Water to | 100.00 |

Melt together the white soft paraffin, cetostearyl alcohol, cetomacragol 1000 and the liquid paraffin. Heat the water to about 60° C., dissolve the methyl and propyl hydroxybenzoate and the benzyl alcohol and add the resulting solution to the melted oil phase. Mix vigorously until cold.

The active compound may be incorporated into the aqueous phase or into the formed emulsion.

| (B) Water in oil emulsion base | % w/w |
|---|---|
| Compound of Example 11 (active compound) | 1-2 |
| Wool alcohols | 3.0 |
| Hard paraffin | 12.0 |
| White soft paraffin | 5.0 |
| Liquid paraffin | 30.0 |
| Water to | 100.0 |

Melt together the wool alcohols and the paraffins. Heat the water to about 60° C. and add to the melted oil phase. Mix vigorously until cold.

The active compound may be incorporated into the water or into the formed emulsion.

| (C) Water soluble (miscible) base | % w/w |
|---|---|
| Compound of Example 11 (active compound) | 1-2 |
| Polyethylene glycol 4000 | 31.5 |
| Polyethylene glycol 400 | 54.0 |
| Stearyl alcohol | 4.5 |
| Water to | 100.0 |

Heat the glycols, stearyl alcohol and water to about 60° C. and mix together until cold. Incorporate the active compound.

EXAMPLE 19

| ORAL TABLET | mg/tablet |
|---|---|
| Compound of Example (active compound) | 200.0 |
| Avicel PH 101 | 200.0 |
| Lactose BP | 87.5 |
| Water q.s. | |
| AcDisol (a cellulose based disintegrant) | 10.0 |
| Magnesium Stearate BP | 2.5 |

| ORAL TABLET | mg/tablet |
|---|---|
| | 500.0 mg |

PROCESS

Mix the active compound, Avicel PH 101 and lactose in a suitable mixer. Granulate with water, grade into a suitable size and dry in a suitable drier. Mix the dried granule with AcDisol and magnesium stearate. Compress on a suitable machine using round N/C tooling.

EXAMPLE 20

| VAGINAL TABLET | mg/tablet |
|---|---|
| Compound of Example 11 (active compound) | 100.0 |
| Anhydrous lactose USP or Emcompress* | 4332.5 |
| Maize starch BP | 45.0 |
| Magnesium stearate BP | 22.5 |
| | 4500.0 mg |

PROCESS

Mix the active compound, anhydrous lactose USP (or Emcompress), maize starch BP and magnesium stearate BP in a suitable mixer. Compress on a suitable machine fitted with almond shaped toolings.

EXAMPLE 21

The following end products are prepared by condensing the stated pyridinium compound and the stated aldehyde in a similar manner to Examples 1 to 11.

| Pyridinium Compound | Aldehyde | End Product |
|---|---|---|
| 2-Methoxy-4-methyl-1-propylpyridinium bromide | 4-Dimethylamino-benzaldehyde | 4-[4-(Dimethylamino)styryl]-2-methoxy-1-propylpyridinium bromide |
| 5-Chloro-2-methyl-1-propylpyridinium bromide | 4-Diethylamino-benzaldehyde | 5-Chloro-2-[4-(Diethylamino)styryl]-1-propyl-pyridinium bromide |
| 2-Methyl-4-nitro-1-propylpyridum bromide | 4-Dimethylamino-benzaldehyde | 2-[4-(Dimethylamino)styryl]-4-nitro-1-propylpyridinium bromide |
| 1-Hexyl-2-methyl-pyridinium chloride | 3-Bromo-4-(dimethylamino)benzaldehyde | 2-[3-Bromo-4-(dimethyl-amino)styryl]-1-hexyl-pyridinium chloride |
| 1-Hexyl-2-methyl-pyridinium bromide | 4-(1-pyrrolidinyl)benzaldehyde | 1-Hexyl-2-[4-(1-pyrrolidinyl)styryl]pyridinium bromide |
| 1-Hexyl-4-methyl-pyridinium bromide | 4-(1-Azacyclo-heptyl)benzaldehyde | 4-[4-(1-Azacycloheptyl)styryl]-1-hexyl-pyridinium bromide |
| 1-Hexyl-4-methyl-pyridinium bromide | 4-(Dimethylamino)-3-nitrobenzaldehyde | 4-[4-(Dimethylamino)-3-nitrostyryl]-1-hexylpyridinium bromide |
| 1-Hexyl-4-methyl-pyridinium bromide | 4-(Dimethylamino)-3-methoxybenz-aldehyde | 4-[4-(Dimethylamino-3-methoxystyryl]-1-hexylpyridinium bromide |
| 1-Hexyl-4-methyl-pyridinium bromide | 4-(Dibenzylamino)benzaldehyde | 4-[4-(Dimethylamino)styryl]-1-hexyl-pyridinium bromide |
| 1-Hexyl-2-methyl-pyridinium bromide | 4-(Dimethylamino)-3-methylbenz-aldehyde | 2-[4-(Dimethylamino)-3-methylstyryl]-1-hexylpyridinium bromide |
| 1-Hexyl-4-methyl-pyridinium bromide | 4-Morpholino-benzaldehyde | 1-Hexyl-4-[4-(morpholino)styryl]pyridinium bromide |
| 1-Hexyl-4-methyl-pyridinium bromide | 4-(Thiomorpholino)benzaldehyde | 1-Hexyl-4-[-4-(thio-morpholino)styryl]pyridinium bromide |
| 1-Hexyl-2-methyl-pyridinium bromide | 4-(4-methyl-piperazin-1-yl)benzaldehyde | 2-[4-(4-methyl-piperazin-1-yl)styryl]-1-hexylpyridinium bromide |
| 1-Hexyl-4-methyl-pyridinium bromide | 4-(3-methyl-piperidino)benz-aldehyde | 1-Hexyl-4-[4-(3-methyl-piperidino)styryl]pyridinium bromide |
| 1-Hexyl-4-methyl-pyridinium bromide | 4-(3-ethyl-4-methylpiperidino)benzaldehyde | 4-[4-(3-ethyl-4-methyl-piperidino)styryl]-1-hexylpyridinium bromide |

A further aspect of the invention resides in the use of compounds containing a cation having formula Ia or Ib and an anion as anti-fungal agents in agriculture or horticulture. Accordingly the invention further provides a method of combating fungal disease in a plant, comprising applying to the plant or seed of the plant or to the locus of the plant or seed (for instance, land in which the plant is growing or to be grown) a compound containing a cation having formula Ia or Ib. The invention further provides an anti-fungal composition comprising a compound containing a cation having formula Ia or Ib as active ingredient and a carrier for the active ingredient. The compositions may be in the form of mixtures with fertilisers or liquid preparations for use as dips or sprays. The most appropriate amount of the active ingredient to be used for horticulture or agriculture applications may be determined experimentally in known manner.

What is claimed is:

1. An anti-fungal composition useful for topical administration, the composition being in the form of an aerosol, a semi-solid pharmaceutical composition or a powder, the composition comprising an anti-fungally useful amount of a compound that contains a cation having the formula Ia or Ib

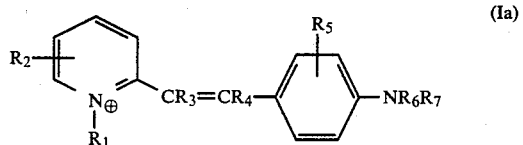

or

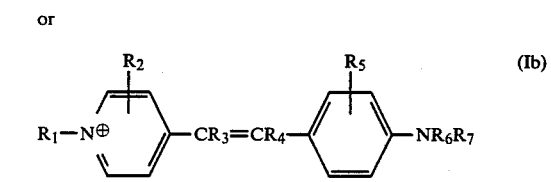

(in which $R_1$ is selected from alkyl containing 3 to 20 carbon atoms and phenyl lower alkyl; $R_2$ and $R_5$ are independently selected from hydrogen, lower alkyl, lower alkoxy, halogen and nitro; $R_3$ and $R_4$ are independently selected from hydrogen and lower alkyl; $R_6$ and $R_7$, when separate, are independently selected from lower alkyl and phenyl lower alkyl; $R_6$ and $R_7$, when joined together, represent a group selected from those having the formula II $$-(CH_2)_2-A-(CH_2)_2-\quad (II)$$

(where A is selected from $-(CH_2)_n-$, O, S and $NR_8$ where n is selected from 0, 1 and 2 and $R_8$ is lower alkyl) and their mono- and di- (lower alkyl) substitution products) and a pharmaceutically acceptable anion in association with a pharmaceutically acceptable carrier.

2. A method of treatment of a subject in need of anti-fungal therapy, which comprises administration of an effective amount of a compound that contains a cation having the formula Ia or Ib

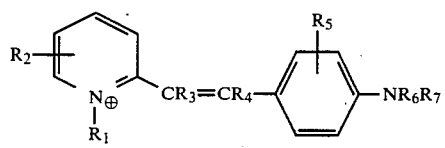

or

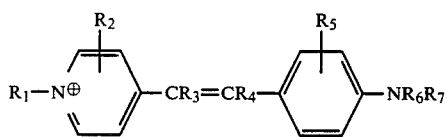

(in which $R_1$ is selected from alkyl containing 3 to 20 carbon atoms and phenyl lower alkyl; $R_2$ and $R_5$ are independently selected from hydrogen, lower alkyl, lower alkoxy, halogen and nitro; $R_3$ and $R_4$ are independently selected from hydrogen and lower alkyl; $R_6$ and $R_7$ when separate, are independently selected from lower alkyl and phenylloweralkyl; and $R_6$ and $R_7$, when joined together, represent a group selected from those having the formula II $$-(CH_2)_2-A-(CH_2)_2-\quad (II)$$

(where A is selected from $-(CH_2)_n-$, O, S and $NR_8$ where n is selected from 0, 1 and 2 and $R_8$ is lower alkyl and their mono- and di- (lower alkyl) substitution products) and a pharmaceutically acceptable anion to the said subject.

3. The method of claim 2, wherein said compound is topically administered.

4. The method of claim 2, wherein said compound contains the cation of formula IB.

5. The method of claim 2, wherein said compound, $R_6$ and $R_7$, when separate, are independently selected from methyl and ethyl and $R_6$ and $R_7$, when joined together, represent $-(CH_2)_5-$.

6. The method of claim 2, wherein the said cation is 2-[4-(dimethylamino)styryl]-1-hexylpyridinium.

7. The method of claim 2, wherein the said cation is 2-[4-(diethylamino)styryl]-1-hexylpyridinium.

8. The method of claim 2, wherein the said cation is 2-[4-(dimethylamino)styryl]-1-dodecylpyridinium.

9. The method of claim 2, wherein the said cation is 2-[4-(diethylamino)styryl]-1-dodecylpyridinium.

10. The method of claim 2, wherein said cation is 1-benzyl-2-[4-(dimethylamino)styryl]pyridinium.

11. The method of claim 2, wherein the said cation is 1-benzyl-2-[4-(diethylamino)styryl]pyridinium.

12. The method of claim 2, wherein said cation is 4-[4-(dimethylamino)styryl]-1-hexylpyridinium.

13. The method of claim 2, wherein the said cation is 4-[4-(diethylamino)styryl]-1-hexylpyridinium.

14. The method of claim 2, wherein the said cation is 4-[4-dimethylamino)styryl]-1-dodecylpyridinium.

15. The method of claim 2, wherein the said cation is 2-[4-(diethylamino)styryl[-5-ethyl-1-propylpyridinium.

16. The method of claim 2, wherein the said cation is 2-[4-(dimethylamino)styryl-5-ethyl-1-propylpyridinium.

17. The method of claim 2, wherein the said cation is 1-dodecyl-2-[4-(piperidino)styryl]pyridinium.

18. The method of claim 2, wherein the said cation is 1-hexyl-2-[4-(piperidino)styryl]pyridinium.

19. The method of claim 2, wherein the said cation is 1-hexyl-4-[4-(piperidino)styryl]pyridinium.

20. The method of claim 2, wherein the said cation is 1-decyl-4-[4-(dimethylamino)styryl]pyridinium.

21. The method of claim 2, wherein the said cation is 1-hexyl-4-[4-(pyrrolidin-1-yl)styryl]pyridinium.

22. The method of claim 2, wherein the said cation is 1-decyl-4-[4-(pyrrolidin-1-yl)styryl]pyridinium.

* * * * *